United States Patent
Jacobson (10) Patent No.: US 9,050,627 B2
(45) Date of Patent: Jun. 9, 2015

(54) SYSTEMS AND METHODS FOR ULTRASONIC POWER MEASUREMENT AND CONTROL OF PHACOEMULSIFICATION SYSTEMS

(75) Inventor: Jon D. Jacobson, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 500 days.

(21) Appl. No.: 13/224,864

(22) Filed: Sep. 2, 2011

(65) Prior Publication Data

US 2013/0057253 A1    Mar. 7, 2013

(51) Int. Cl.
| | | |
|---|---|---|
| G01R 25/00 | (2006.01) | |
| H03D 13/00 | (2006.01) | |
| B06B 1/02 | (2006.01) | |
| A61F 9/007 | (2006.01) | |

(52) U.S. Cl.
CPC ........... *B06B 1/0253* (2013.01); *A61F 9/00745* (2013.01); *B06B 2201/76* (2013.01)

(58) Field of Classification Search
CPC .......................... G01R 21/133; G01R 19/175
USPC .......... 324/76.77, 76.11, 76.39, 76.52, 76.82, 324/76.83, 91; 702/72
See application file for complete search history.

(56) References Cited

U.S. PATENT DOCUMENTS

| | | | |
|---|---|---|---|
| 2,434,480 A | 1/1948 | Anderson | |
| 3,674,934 A * | 7/1972 | Gooding et al. | 375/336 |
| 3,857,387 A | 12/1974 | Shock | |
| 3,941,122 A | 3/1976 | Jones | |
| 4,184,510 A | 1/1980 | Murry et al. | |
| 4,343,111 A | 8/1982 | Inoue | |
| 4,414,675 A * | 11/1983 | Comroe | 375/274 |
| 4,669,095 A * | 5/1987 | Hall | 375/336 |

(Continued)

FOREIGN PATENT DOCUMENTS

| | | |
|---|---|---|
| CA | 2242328 A1 | 5/1998 |
| DE | 19940712A 1 | 3/2001 |

(Continued)

OTHER PUBLICATIONS

International Search Report and Written Opinion for Application No. PCT/US2012/052992, mailed on Jul. 16, 2013, 12 pages.

(Continued)

*Primary Examiner* — Huy Q Phan
*Assistant Examiner* — Giovanni Astacio-Oquendo
(74) *Attorney, Agent, or Firm* — Abbott Medical Optics Inc.

(57) ABSTRACT

A method for determining the voltage current phase relationship of a piezoelectric phacoemulsification handpiece generally includes the steps of obtaining an analog AC voltage signal corresponding to the operating AC voltage of a piezoelectric handpiece along with an analog AC current signal corresponding to the operating AC current of the piezoelectric handpiece. Using reference detection circuits, a digital voltage signal and a digital current signal is produced. A synchronous sample clock is taken that has a frequency that is $2^N$ times faster than the frequency of the operating ultrasonic handpiece (i.e., driving frequency), where N is the number of digital bits allocated to the sample clock. This clock measures the time between onsets of a voltage and current cycle. This time value equates to the phase time delta between the two signals. Dividing the synchronous sample clock to obtain the driving frequency ensures the signals are synchronous.

20 Claims, 11 Drawing Sheets

(56) References Cited

U.S. PATENT DOCUMENTS

| | | |
|---|---|---|
| 4,736,130 A | 4/1988 | Puskas |
| 4,808,948 A | 2/1989 | Patel et al. |
| 4,827,911 A | 5/1989 | Broadwin et al. |
| 4,952,834 A | 8/1990 | Okada |
| 4,954,960 A | 9/1990 | Lo et al. |
| 4,970,656 A | 11/1990 | Lo et al. |
| 4,983,901 A | 1/1991 | Lehmer |
| 5,001,649 A | 3/1991 | Lo et al. |
| 5,091,656 A | 2/1992 | Gahn |
| 5,209,221 A | 5/1993 | Riedlinger |
| 5,213,569 A | 5/1993 | Davis |
| 5,242,404 A | 9/1993 | Conley et al. |
| 5,249,121 A | 9/1993 | Baum et al. |
| 5,268,624 A | 12/1993 | Zanger |
| 5,279,547 A | 1/1994 | Costin |
| 5,318,563 A | 6/1994 | Malis et al. |
| 5,331,951 A | 7/1994 | Kepley |
| 5,342,293 A | 8/1994 | Zanger |
| 5,370,602 A | 12/1994 | Kepley |
| 5,388,569 A | 2/1995 | Kepley |
| 5,403,307 A | 4/1995 | Zelman |
| 5,405,614 A | 4/1995 | D'Angelo et al. |
| 5,406,503 A | 4/1995 | Williams, Jr. et al. |
| 5,417,246 A | 5/1995 | Perkins et al. |
| 5,431,664 A | 7/1995 | Ureche et al. |
| 5,453,087 A | 9/1995 | Malinowski |
| 5,520,633 A | 5/1996 | Costin |
| 5,534,741 A | 7/1996 | Smith |
| 5,547,459 A | 8/1996 | Kaufman et al. |
| 5,582,578 A | 12/1996 | Zhong et al. |
| 5,591,127 A | 1/1997 | Barwick, Jr. et al. |
| 5,692,166 A * | 11/1997 | Milhizer et al. ............ 713/400 |
| 5,700,240 A | 12/1997 | Barwick, Jr. et al. |
| 5,733,256 A | 3/1998 | Costin |
| 5,738,677 A | 4/1998 | Colvard et al. |
| 5,739,724 A * | 4/1998 | Alexandre et al. ........... 331/1 R |
| 5,766,146 A | 6/1998 | Barwick, Jr. |
| 5,797,494 A | 8/1998 | Balling et al. |
| 5,800,365 A | 9/1998 | Zhong et al. |
| 5,808,396 A | 9/1998 | Boukhny |
| 5,832,412 A | 11/1998 | Guez |
| 5,836,959 A | 11/1998 | Seibel et al. |
| 5,852,794 A | 12/1998 | Staggs |
| 5,873,885 A | 2/1999 | Weidenbenner |
| 5,938,677 A | 8/1999 | Boukhny et al. |
| 5,979,494 A | 11/1999 | Perkins et al. |
| 5,984,882 A | 11/1999 | Rosenschein et al. |
| 5,997,528 A | 12/1999 | Bisch et al. |
| 6,010,496 A | 1/2000 | Appelbaum et al. |
| 6,083,193 A | 7/2000 | Kadziauskas et al. |
| 6,086,598 A | 7/2000 | Appelbaum et al. |
| 6,117,126 A | 9/2000 | Appelbaum et al. |
| 6,155,975 A | 12/2000 | Urich et al. |
| 6,161,545 A | 12/2000 | Chow |
| 6,175,180 B1 | 1/2001 | Angelini et al. |
| 6,193,683 B1 | 2/2001 | Ludin et al. |
| 6,203,516 B1 | 3/2001 | Kepley |
| 6,251,113 B1 | 6/2001 | Appelbaum et al. |
| 6,261,297 B1 | 7/2001 | Kadziauskas et al. |
| 6,319,220 B1 | 11/2001 | Bylsma |
| 6,391,020 B1 | 5/2002 | Kurtz et al. |
| 6,391,042 B1 | 5/2002 | Cimino |
| 6,394,974 B1 | 5/2002 | Kadziauskas et al. |
| 6,425,883 B1 | 7/2002 | Urich et al. |
| 6,428,531 B1 | 8/2002 | Visuri et al. |
| 6,443,900 B2 | 9/2002 | Adachi et al. |
| 6,452,120 B1 | 9/2002 | Chen |
| 6,452,123 B1 | 9/2002 | Chen |
| 6,452,883 B2 | 9/2002 | Chan |
| 6,487,447 B1 | 11/2002 | Weimann et al. |
| 6,506,176 B1 | 1/2003 | Mittelstein et al. |
| 6,589,204 B1 | 7/2003 | Sussman et al. |
| 6,610,052 B2 | 8/2003 | Furumoto |
| 6,629,948 B2 | 10/2003 | Rockley et al. |
| 6,699,212 B1 | 3/2004 | Kadziauskas et al. |
| 6,726,679 B1 | 4/2004 | Dick et al. |
| 6,733,491 B2 | 5/2004 | Kadziauskas et al. |
| 6,780,165 B2 | 8/2004 | Kadziauskas et al. |
| 6,808,396 B2 | 10/2004 | Kawaguchi et al. |
| 6,884,252 B1 | 4/2005 | Urich et al. |
| 6,890,332 B2 | 5/2005 | Truckai et al. |
| 6,896,674 B1 | 5/2005 | Woloszko et al. |
| 6,908,472 B2 | 6/2005 | Wiener et al. |
| 6,939,317 B2 | 9/2005 | Zacharias |
| 6,962,583 B2 | 11/2005 | Kadziauskas et al. |
| 7,077,820 B1 | 7/2006 | Kadziauskas et al. |
| 7,169,123 B2 | 1/2007 | Kadziauskas et al. |
| 7,193,521 B2 | 3/2007 | Moberg et al. |
| 7,316,664 B2 | 1/2008 | Kadziauskas et al. |
| 7,485,106 B2 | 2/2009 | Kadziauskas et al. |
| 2001/0003155 A1 | 6/2001 | Rockley et al. |
| 2001/0003295 A1 | 6/2001 | Langlotz et al. |
| 2001/0003385 A1 | 6/2001 | Ise |
| 2001/0039389 A1 | 11/2001 | Sakurai et al. |
| 2002/0049555 A1 | 4/2002 | Wiener |
| 2002/0052600 A1 | 5/2002 | Davison et al. |
| 2002/0072741 A1 | 6/2002 | Sliwa et al. |
| 2002/0082793 A1 | 6/2002 | Kadziauskas et al. |
| 2003/0097083 A1* | 5/2003 | Anderson et al. ............... 601/2 |
| 2004/0092921 A1 | 5/2004 | Kadziauskas et al. |
| 2004/0092922 A1* | 5/2004 | Kadziauskas et al. .......... 606/27 |
| 2004/0193182 A1 | 9/2004 | Yaguchi et al. |
| 2005/0020967 A1 | 1/2005 | Ono |
| 2005/0054971 A1 | 3/2005 | Steen et al. |
| 2005/0209560 A1 | 9/2005 | Boukhny et al. |
| 2005/0209621 A1 | 9/2005 | Gordon et al. |
| 2005/0288665 A1 | 12/2005 | Woloszko |
| 2006/0149301 A1 | 7/2006 | Claus |
| 2006/0195077 A1 | 8/2006 | Kadziauskas et al. |
| 2006/0264809 A1 | 11/2006 | Hansmann et al. |
| 2007/0056596 A1 | 3/2007 | Fanney et al. |
| 2007/0073214 A1 | 3/2007 | Dacquay et al. |
| 2007/0078379 A1 | 4/2007 | Boukhny et al. |

FOREIGN PATENT DOCUMENTS

| | | |
|---|---|---|
| EP | 270819 A2 | 6/1988 |
| EP | 270819 A3 | 1/1989 |
| EP | 336620 A2 | 10/1989 |
| EP | 336620 B1 | 12/1993 |
| EP | 1351631 A1 | 10/2003 |
| EP | 1537840 A1 | 6/2005 |
| JP | 63315049 A | 12/1988 |
| JP | 2204337 A2 | 8/1990 |
| JP | 5038343 A2 | 2/1993 |
| JP | 6183762 A2 | 7/1994 |
| JP | 6189972 A2 | 7/1994 |
| JP | 9313496 A2 | 12/1997 |
| JP | 2001161740 A2 | 6/2001 |
| JP | 2002087836 A2 | 3/2002 |
| JP | 2002233534 A2 | 8/2002 |
| WO | WO9520374 A1 | 8/1995 |
| WO | WO9808442 A1 | 3/1998 |
| WO | WO0051508 A1 | 9/2000 |
| WO | WO0064388 A1 | 11/2000 |
| WO | WO0113838 A1 | 3/2001 |
| WO | WO02056806A 1 | 7/2002 |
| WO | WO2005092023A 2 | 10/2005 |

OTHER PUBLICATIONS

Devine M.D., et al., "How to Set the Dials," Phacoemulsification Surgery, 1991, pp. 7-28.
European Search Report for Application No. EP07011327, mailed on Aug. 6, 2007, 2 pages.
International Preliminary Examination Report for Application No. PCT/US00/10989, mailed on Jul. 13, 2001, 9 pages.
International Preliminary Examination Report for Application No. PCT/US02/00471, mailed on Nov. 19, 2002, 2 pages.
International Preliminary Report on Patentability and Written Opinion for Application No. PCT/US2004/32690, mailed on Apr. 10, 2006, 6 pages.
International Search Report for Application No. PCT/US00/10989, mailed on Aug. 9, 2000, 3 pages.

(56) References Cited

OTHER PUBLICATIONS

International Search Report for Application No. PCT/US02/00471, mailed on May 22, 2002, 3 pages.
International Search Report for Application No. PCT/US2004/32690, mailed on Jan. 25, 2005, 3 pages.
International Search Report for Application No. PCT/US98/01004, mailed on Jun. 9, 1998, 2 pages.
"Ocusystem Operation Manual, May 1995, 79 pages,".
"Pulsar cuts phaco time, boots efficiency in cataract removal; Ophthalmology Times: Aug. 15, 1986; 1 page, 11 (16), Harcourt Brace Jovanovich, Inc,".
Supplementary European Search Report for Application No. EP01989937, mailed on Jul. 6, 2005, 2 pages.
Taylor W.F., et al., "Intraoperative Troubleshooting Of An Advanced Phacoemulsification System," The Surgial Technologist, 1985, vol. 17 (2), pp. 11-14.

\* cited by examiner

SYSTEMS AND METHODS FOR ULTRASONIC POWER MEASUREMENT AND CONTROL OF PHACOEMULSIFICATION SYSTEMS

FIELD OF THE INVENTION

The field of the invention relates to systems and methods for cataract surgery, and more particularly to systems and methods for tuning a piezoelectric phacoemulsification handpiece. Even more specifically, the field of invention relates to improved systems and methods for determining phase angle between voltage applied to a piezoelectric transducer and the current drawn by the piezoelectric transducer.

BACKGROUND OF THE INVENTION

A number of medically recognized techniques are utilized for cataractous lens removal based on, for example, phacoemulsification, mechanical cutting or destruction, laser treatments, water jet treatments, and so on.

Figure 1A:
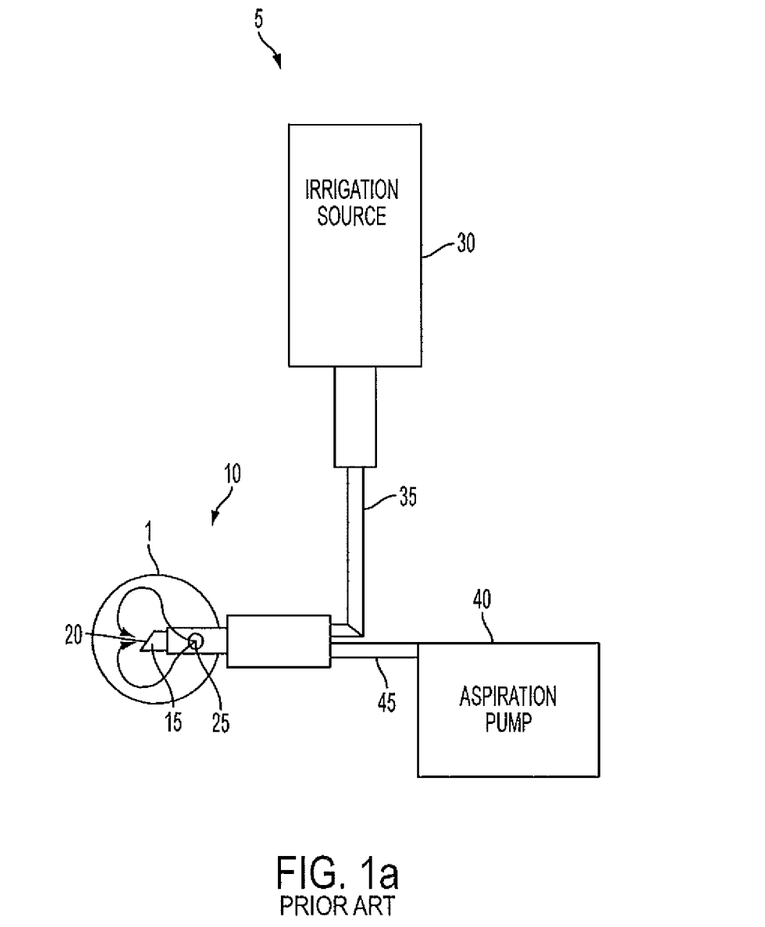
FIG. 1a is a diagram of a phacoemulsification system known in the art.

The phacoemulsification method includes emulsifying, or liquefying, the cataractous lens with ultrasonic power and then removing the emulsified material out of the eye. A phacoemulsification system 5 known in the art is shown in FIG. 1. The system 5 generally includes a phacoemulsification handpiece 10 having a hollow needle 15 at the distal tip (shown within the anterior chamber of the patient's eye 1) that is ultrasonically vibrated to emulsify the cataractous lens within the patient's eye 1. The system 5 typically includes an electronic control interconnected with handpiece 10 by an electric cable for powering and controlling the piezoelectric transducer. The handpiece 10 further includes an irrigation port 25 proximal to the distal tip of the needle 15 for providing irrigation fluid from an irrigation source 30 to the handpiece 10 via an irrigation line 35, and an aspiration port 20 at the distal tip of the needle 15, which is coupled to an aspiration pump 40 via an aspiration line 45 for aspirating fluid from eye 1 through the handpiece 10.

Figure 1B:
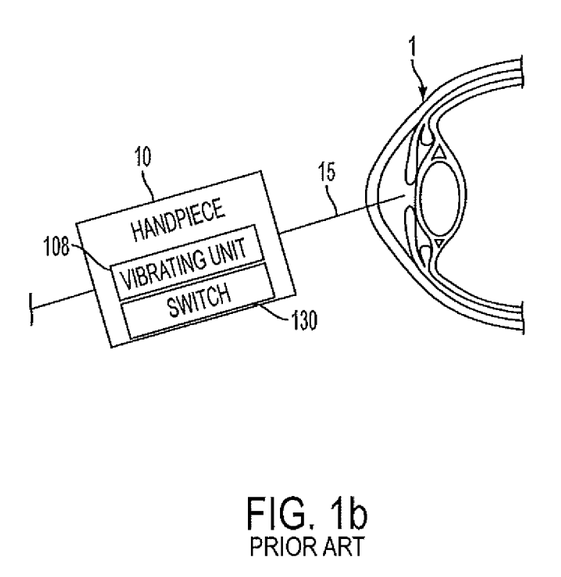
FIG. 1b is a diagram of a phacoemulsification handpiece known in the art.

The hollow needle 15 is generally driven or excited by an applied AC voltage creating a piezoelectric effect in crystals. As is known in the art, this piezoelectric effect may provide either a longitudinal motion or a mix of longitudinal with transversal motions of the needle 15 to affect different desired cutting movements. Referring to FIG. 1b, the handpiece 10 may further include a vibrating unit 108 that is configured to ultrasonically vibrate the needle 15. The vibrating unit 108, which may include, e.g., a piezoelectric crystal, vibrates the needle 15 according to one or more parameters, such as frequency, pulse width, shape, size, duty cycle, amplitude, and so on. The motion of the vibrating unit 108 is amplified by a mechanically resonant system within the handpiece 10, such that the motion of the needle 15 is dependent, inter alia, upon the frequency at which the vibrating unit 108 is driven. The maximum motion of the needle 15 occurs at a resonant frequency. In part, this resonant frequency is dependent on the mass of needle 15 interconnected with the handpiece 10 that is vibrated by the vibrating unit 108.

Ultrasonic power of handpiece 10 generally consists of two parts: (1) a sine wave representing the voltage applied to the handpiece 10, and (2) the waveform representing the resultant current into the handpiece.

In purely capacitive circuits, there is a 90-degree phase angle between a sine wave representing the voltage applied to the handpiece 10 and the resultant current into the handpiece 10. In this case, the resultant current waveform leads the applied voltage waveform by 90-degrees (i.e., $\phi$ equals -90 degrees). Similarly, in purely inductive circuits, there is a 90-degree phase angle between the current and voltage such that the resultant current waveform lags the voltage waveform by 90-degrees (i.e., $\phi$ equals +90 degrees). Finally, for purely resistive circuits, $\phi$ equals 0-degrees.

Phacoemulsification handpieces typically operate in a range of frequencies between approximately 25 kHz to about 65 kHz. For each handpiece, an operational frequency window can be characterized by the handpiece impedance and phase. This frequency window is bounded by an upper frequency and lower cutoff frequency such that frequencies outside the upper and lower cutoffs have an electrical phase equal to -90-degrees. The center of this frequency window is typically the point where the handpiece electrical power reaches a maximum value.

The power transfer efficiency of handpiece 10 is defined by the formula $(V*I)(\cos \phi)$. Accordingly, the most efficient handpiece power operating point occurs when the phase angle between the voltage applied to the handpiece and the resultant current into the handpiece is closest to $\phi$ degrees.

In order to maintain optimum handpiece power transfer efficiency, it is important to control the frequency of the phacoemulsification handpiece to achieve a phase value as close to zero (0) degrees as possible. However, controlling optimum power transfer efficiency is complicated by the fact that during operation, the phase angle of an ultrasonic handpiece is also dependent on the load of the transducer. This occurs through the mechanically resonant system including the handpiece needle 15. Specifically, when handpiece needle 15 comes into contact with tissue and fluids within eye 1, a load is created on the piezoelectric crystals with concomitant change in the operating phase angle.

As is well known, for these various surgical techniques, it is necessary to effect constant energy transfer into the tissue of the eye by the phaco handpiece regardless of loading effects. This can be accomplished by determining and measuring the phase angle at all times during operation of the handpiece in order to adjust the driving circuitry to achieve an optimum phase angle. For example, see U.S. Pat. No. 5,852,794 to Staggs et. al, filed Jan. 22, 1997 for a "Multiple Frequency Unambiguous Phase Detector for Phacoemulsification System" ("Staggs"), which is hereby incorporated by reference in its entirety by specific reference hereto. During phacoemulsification, it is possible to provide automatic tuning of a handpiece by monitoring the handpiece electrical signals and adjusting the frequency to maintain consistency with selected parameters.

Phase detection is the process of applying two electrical periodic signals of similar frequency into an electrical circuit that generates a phase difference, expressed in electrical degrees or time, between the two signals referenced to the same point in time. Conventional control circuitry, typically referred to as a phase detector, exists to measure the phase between the voltage and the current. Voltage generated by a phase detector is usually time averaged by an electronic circuit or sampled by an analog to digital (A/D) convertor and then averaged digitally. An averaged signal helps to reject some noise and can be read by a conventional voltage meter or used by a microprocessor. However, as mentioned above, phase shift is dependent on the operating frequency of the handpiece. Additionally, air and time delay in the measurement requires complex calibration circuitry in order to provide responsive tuning of the handpiece.

For use with a single frequency, the standard technique for measuring electrical phase has been to read a voltage that is proportional to the signal phase and also to frequency. This technique allows calibration for use with a single frequency. However, changing the frequency would cause the calibration data to be incorrect.

For multiple frequency uses, a typical approach has been to use two discrete analog integrators and an A/D convertor to generate phase data independent of the operating frequency. In particular, one integrator concurrently measures the period of a complete signal cycle while a second integrator measures the time between the voltage and current clock edges. Together the measurements are fed into an A/D convertor for use in a micro-controller (an example of such a system is described in U.S. Pat. No. 5,852,794 to Staggs et. al, filed Jan. 22, 1997 for a "Multiple Frequency Unambiguous Phase Detector for Phacoemulsification System"). Nevertheless, this system also involves some hardware calibration. For example, the two matched discrete analog integrators are susceptible to system performance variations due to component tolerances. Reducing variations involves matching component values as closely as possible in order to regulate drift of the individual circuits.

Accordingly, an improved system and method for measuring analog drive voltages and current for ultrasonic power control through phase manipulation is desirable.

SUMMARY OF THE INVENTION

The field of the invention relates to systems and methods for cataract surgery, and more particularly to systems and methods for tuning a piezoelectric phacoemulsification handpiece. Even more specifically, the field of invention relates to improved systems and methods for determining phase angle between voltage applied to the piezoelectric transducer and the current drawn by the piezoelectric transducer. In one embodiment, a method for determining the voltage current phase relationship of a piezoelectric phacoemulsification handpiece generally includes the steps of obtaining an analog AC voltage signal corresponding to the operating AC voltage of a piezoelectric handpiece along with an analog AC current signal corresponding to the operating AC current of the piezoelectric handpiece.

From the AC voltage signal, using a reference detection circuit, a digital voltage signal is produced whose logical levels correspond to the AC voltage transitions. Additionally, onset of a voltage cycle is obtained. More particularly, the onset may be determined on an AC voltage transitioning edge.

From the AC current signal, using a reference detection circuit, a digital current signal is produced whose logical levels correspond to the AC current transitions. Additionally, onset of a current cycle is obtained. More particularly, the onset may be determined on an AC current transitioning edge.

A synchronous sample clock is taken that has a frequency that is $2^N$ times faster than the frequency of the operating ultrasonic handpiece (i.e., driving frequency), where N is the number of digital bits allocated to the sample clock.

After the onset of the voltage cycle, the synchronous sample clock measures the time necessary until the onset of the current cycle. This time value equates to the phase time delta between the two signals. Dividing the synchronous sample clock to obtain the driving frequency ensures the signals are synchronous. Further dividing the end count value into 360° results in the phase shift between the two signals in degrees that is independent of the operating frequency.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

In order to better appreciate how the above-recited and other advantages and objects of the inventions are obtained, a more particular description of the embodiments briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

DETAILED DESCRIPTION OF THE PREFERRED EMBODIMENTS

As described above, conventional phase detection is the process of applying two periodic signals of similar frequency into an electrical circuit that generates a voltage proportional to the phase difference between the two signals. Additionally, automatic tuning of an electrical device, as hereinabove briefly mentioned, may be accomplished by monitoring the two periodic signals and adjusting the frequency to maintain a consistency with selected parameters. For example, the drive voltage of a phacoemulsification handpiece 10 can be increased to compensate while a load is detected at the tip of the handpiece 10 and decreased when the load is removed.

Figure 2:
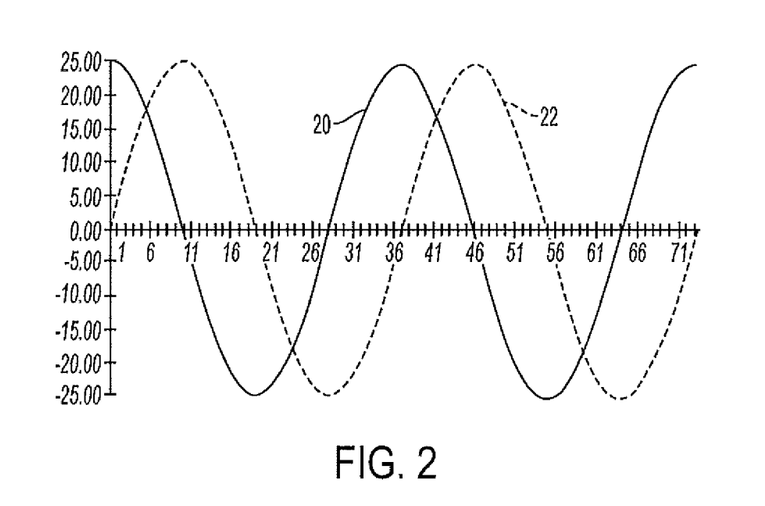
FIG. 2 is a plot of the 90-degree phase shift between the sinusoidal wave representation of the AC voltage applied to a piezoelectric phacoemulsification handpiece and the resultant current into the handpiece.

Generally, when the frequency applied to a phacoemulsification handpiece 10 is significantly higher or lower than resonance (e.g., falls outside of typical operation range 25 kHz-65 kHz), the handpiece 10 electrically responds as a capacitor. In particular, there is a 90-degree phase angle between the voltage applied and the resultant current waveforms. Turning to FIG. 2, an exemplary plot of such a 90-degree phase shift between two electrical periodic signals is shown.

Solid curve 20 represents a sine wave that corresponds, for example, to the driving voltage of a phacoemulsification handpiece 10. Dashed curve 22 also represents a sine wave that corresponds, for example, to the resultant current of the phacoemulsification handpiece 10. The shift between the two curves represents a 90-degree phase angle.

Figure 3:
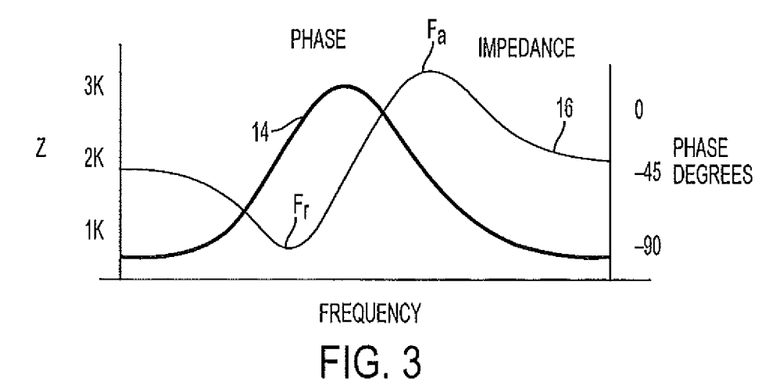
FIG. 3 is a plot of the phase relationship and the impedance of a typical piezoelectric phacoemulsification handpiece.

Similar to the dependence of the phase angle of a phacoemulsification handpiece on frequency, the impedance of the handpiece is correspondingly reactive with the operating frequency. FIG. 3 illustrates the phase relationship and the impedance of an exemplary piezoelectric phacoemulsification handpiece as a function of frequency. Curve 14 represents the current voltage phase difference of the handpiece as a function of frequency and curve 16 represents the change of impedance of the handpiece as a function of frequency. During typical phacoemulsification use, as the operating frequency varies, the impedance of the handpiece may vary between a low impedance $F_r$ and a higher impedance $F_a$. Similarly, the voltage and current waveforms vary in phase.

As mentioned above, for current systems using phase angle as a tuning parameter, varying the operating frequency may affect whether a precise phase measurement is obtained. As a result, additional calibration is required to reduce inaccuracies of phase measurement including additional signal processing and/or circuitry components. However, potential sources of error associated with separate hardware processing may be introduced.

Figure 4A:
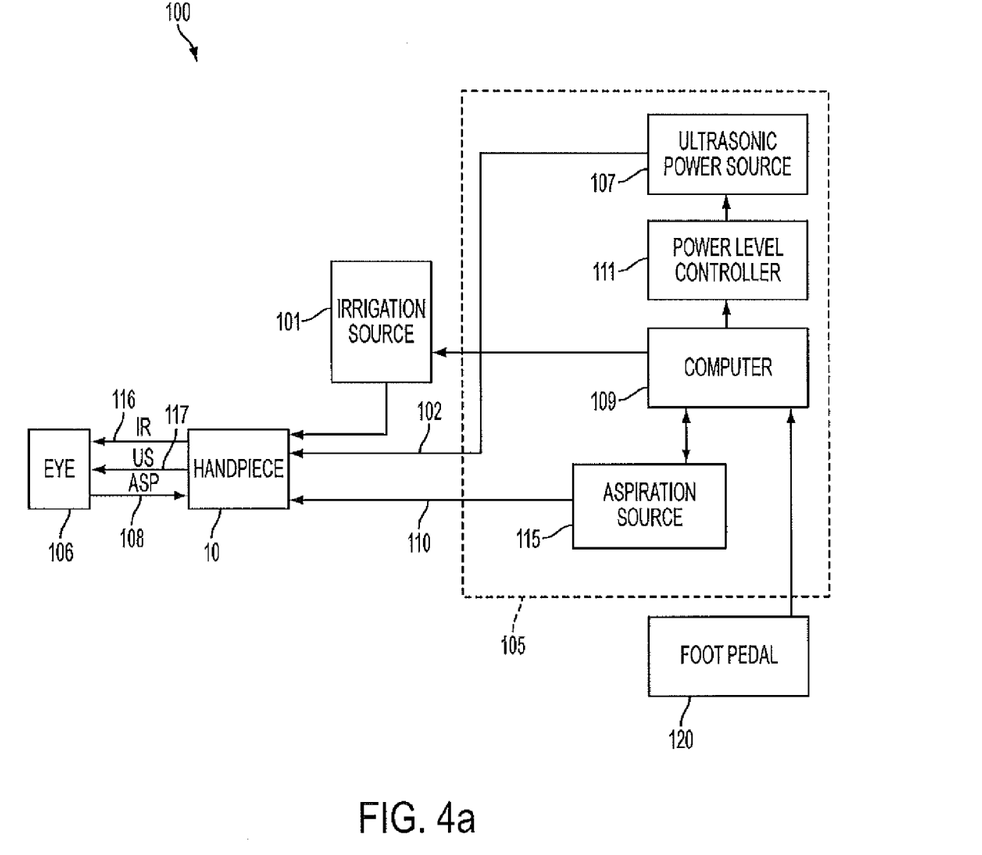
FIG. 4a is a diagram of a phacoemulsification system suitable for performing a method in accordance with the present invention.

Referring to FIG. 4a, an exemplary system 100 that allows for tuning of a phacoemulsification handpiece 10 is further illustrated in block diagram form. The system 100 has a control unit 105, indicated by the dashed lines in FIG. 4a, that includes a source of ultrasonic power 107 coupled to a handpiece 10 via line 102. A microprocessor computer 109 provides control outputs to ultrasonic power level controller 111 that controls the ultrasonic power source 107. The control unit 105 further includes an aspiration source 115 applied to handpiece 10 via line 110 and an irrigation fluid source 101 that is fluidly coupled to the handpiece 10. The block representation of the handpiece 10 includes a needle and electrical means (not shown), typically a piezoelectric crystal, for ultrasonically vibrating the needle. The handpiece/needle 10 is used to apply the elements above to a patient's eye, or affected area or region, indicated diagrammatically by block 106. A foot pedal 120 coupled to the computer 109 may be utilized to enable a surgeon/operator to control the irrigation source 101, the power source 107, and the aspiration source 115.

Figure 4B:
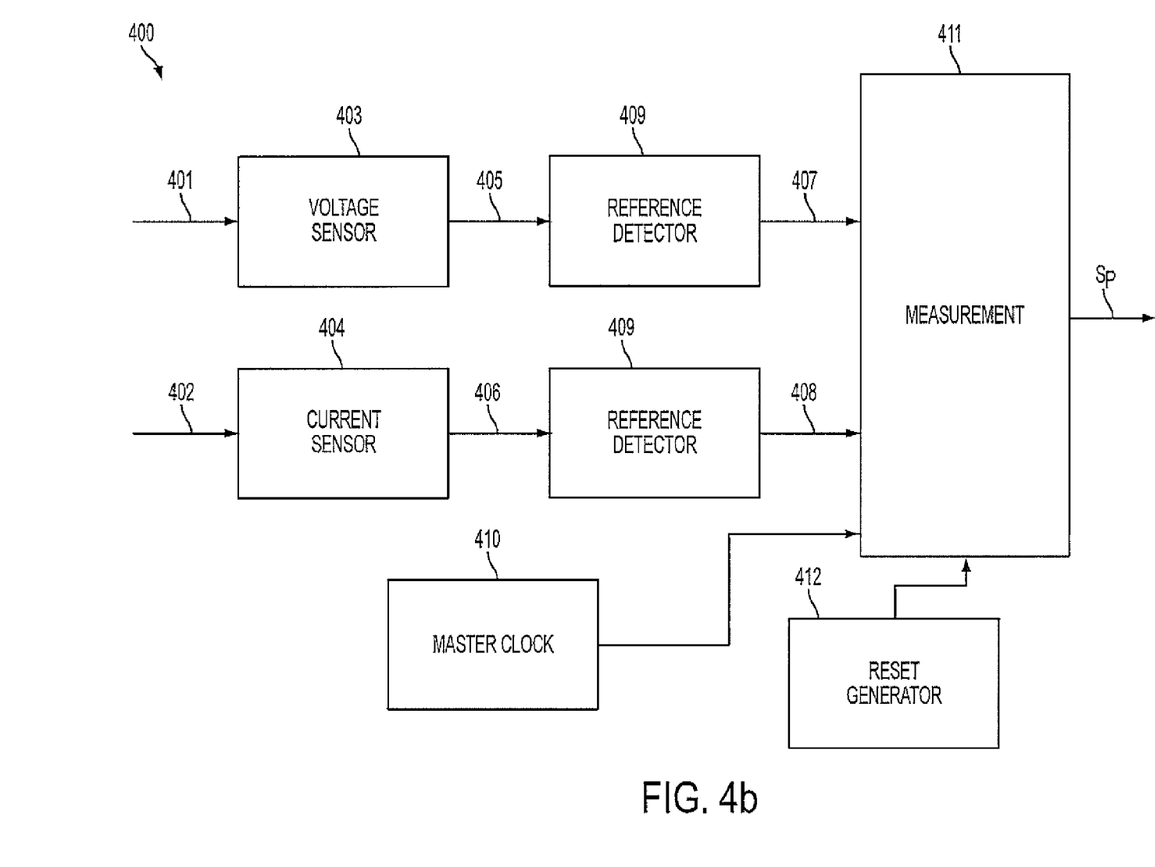
FIG. 4b is a functional block diagram of an improved phase measurement counter suitable for performing a method in accordance with the present invention.

Within the control unit 105, the microprocessor computer 109 may provide control outputs to ultrasonic power level controller 111 based on, for example, phase angle. Turning to FIG. 4b, an improved phase detector 400 suitable for performing the method in accordance with the present invention is shown. Each of the function blocks shown comprises conventional state of the art circuitry of typical design and components for producing the function represented by each block as hereinafter described.

The voltage input 401 and current input 402 from a phacoemulsification handpiece (not shown) are converted to appropriate signals using a voltage sensor 403 (e.g., via attenuation, transformer isolation, signal buffering, and similar voltage sensing techniques as those of ordinary skill in the art can appreciate) on the voltage signal to the phacoemulsification handpiece, and a current sensor 404 (e.g., a current sense resistor) and fixed gain amplifier for the handpiece current. Alternatively, current sensor 404 is not limited to measuring the potential difference (i.e., voltage drop) associated with a current through a known resistance, but may also include, for example, measuring the magnetic field surrounding a conductor carrying the handpiece current. Thereafter, an AC voltage signal 405 and an AC current signal 406 are passed to reference detectors 409 (e.g., zero-cross detectors, peak detectors, and trough detectors), which convert the analog representations of the phacoemulsification voltage and current to digital signals 407, 408.

Figure 5:
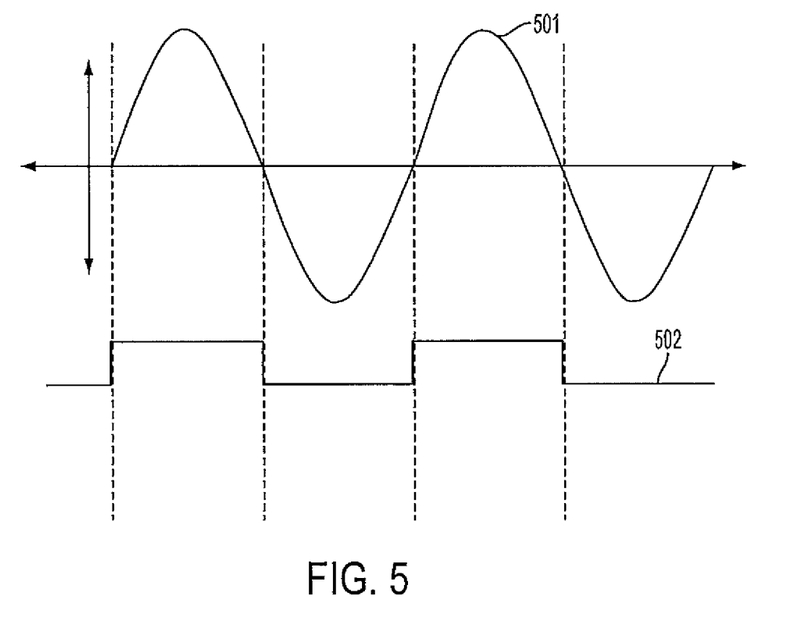
FIG. 5 is a diagram showing an exemplary conversion between an analog signal to a digital signal.

The digital signals 407 and 408 each represent a logical level square wave with transitioning edges at the AC reference value. With reference to FIG. 5, an example of an AC waveform 501, for example, representing AC voltage or AC current, is shown converted to a logical level signal 502 where the logical highs correspond to positive AC measurements of waveform 501 and transitioning edges at the AC zero value.

Subsequently, referring back to FIG. 4b, digital signals 407 and 408 can be measured within measurement circuit 411. A master clock 410 is fed into circuit 411 for timing of the phase measurement. The clock 410 uses a signal that is $2^N$ times faster than the frequency of the AC current signal, where N is the number of bits allocated to the master clock 410 in system 100. For example, using an 8-bit measurement, master clock 410 can be 256 times faster (e.g., approximately 9.7 MHz), than the frequency of the AC current signal (e.g., approximately 38 kHz). However, it is also appreciated by one of ordinary skill in the art that a higher speed clock may be used, for example, a clock that is 1,024 times faster than the driving frequency for improved resolution. In a preferred embodiment, the system will use between 2-16 bits, preferably 8-12 bits, and more preferably 12-16 bits.

A reset generator 412 is also fed into circuit 411 for resetting internal control signals within circuit 411 (not shown) and the master clock 410. Input to the microprocessor computer 109 can provide a manual reset switch to generator 412. More preferably, generator 412 is automatically triggered to reset, for example, master clock 410, by the voltage and current signals upon completion of a phase measurement.

Figure 4C:
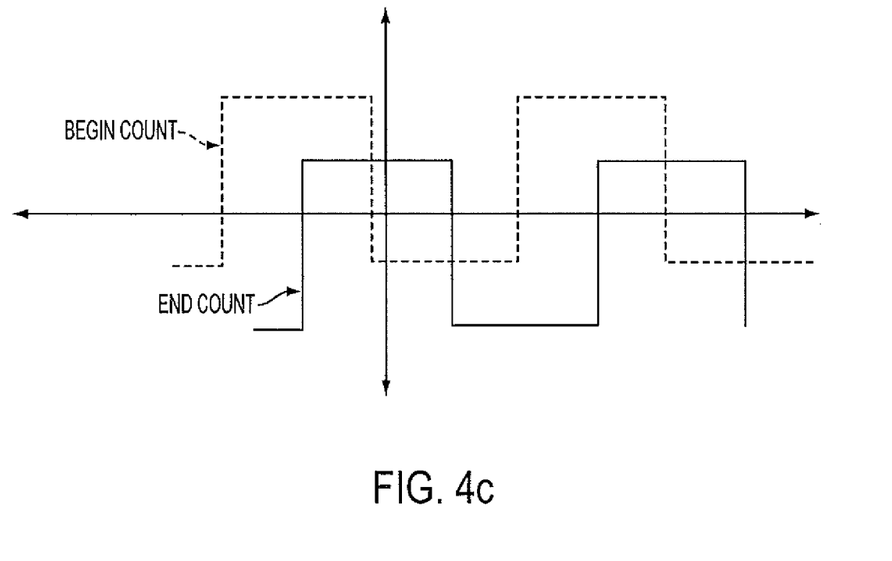
FIG. 4c is a plot showing an exemplary timing process between two digital logic level signals.
Figure 4D:
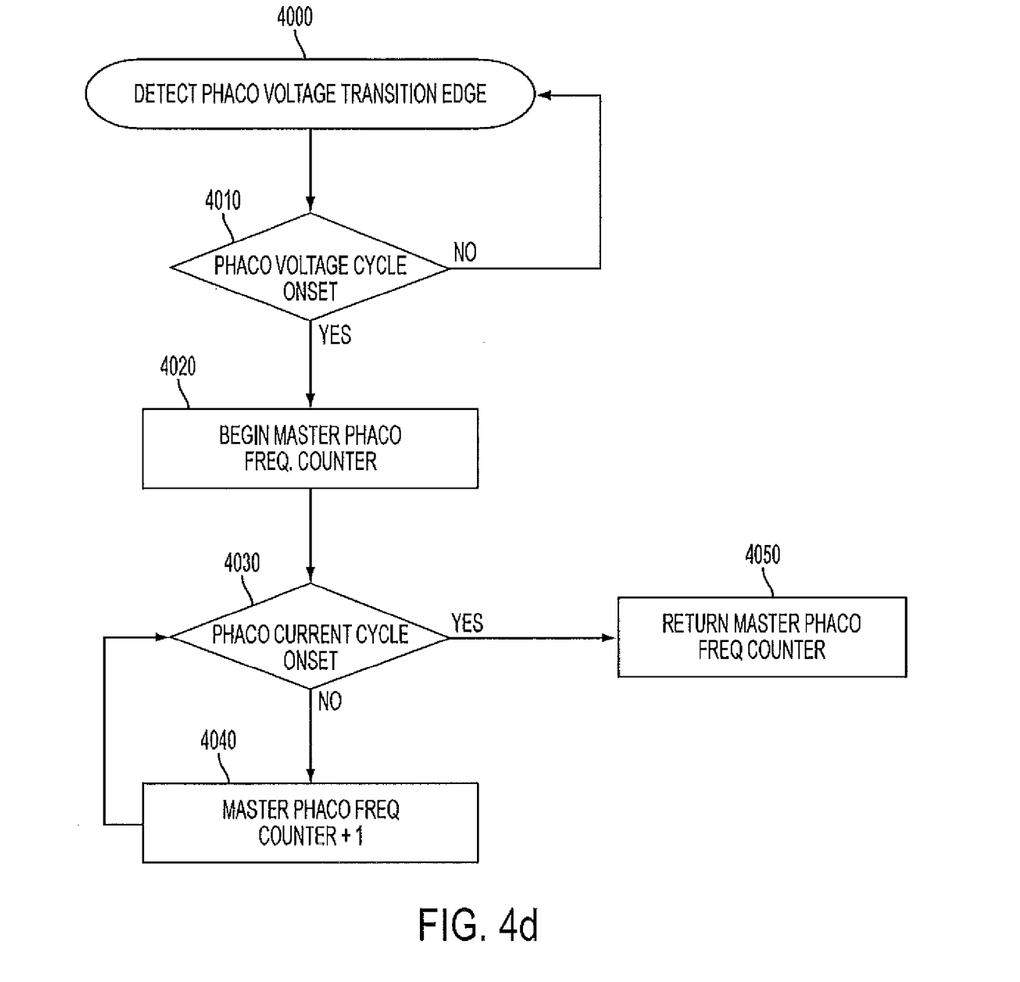
FIG. 4d is a flowchart of a process in accordance with a preferred embodiment of the present invention.

Turning to FIG. 4d, the phase detector 400 will first wait for a transition of signal 407 (start block 4000). Upon a transition of digital signal 407 representing an onset of a voltage cycle (decision block 4010), measurement circuit 411 begins a counter to determine the time delta $S_P$ necessary for the digital signal 408 to transition representing the onset of a current cycle (action block 4020). Accordingly, the counter ends upon a transition of digital signal 408 (decision block 4030) and (action block 4040).

The timing of this counter is illustrated in FIG. 4c, which shows the counter beginning on a transition of the first input and ending on the transition of the second input. Although FIG. 4c illustrates the counter beginning and ending on the rising edges of the first and second inputs, respectively, one of ordinary skill in the art would appreciate the counter can also begin and end on a falling edge or a combination of both a rising and a falling edge of the input signals. The counter determines the number of higher speed clock 410 periods occurring between transitions of signals 407 and 408 (action block 4050). This resulting time delta $S_P$ represents a phase measurement between the two AC waveforms.

The output $S_P$ is then fed to a system controller (not shown) that can divide the higher speed master clock to obtain the frequency of the operating phacoemulsification drive signals. For example, a master clock running at approximately 9.7 MHz can be divided by 256 (i.e., 8 bits) to obtain the ultrasonic frequency of approximately 38 kHz. Accordingly, dividing the higher speed clock to generate the ultrasonic clock ensures that the phase measurement is synchronous regardless of the driving frequency. This signal represents a measurement between 0 and 359 degrees of phase.

The advantage of using this approach is that the system is provided with a precise real time digital phase signal measurement independent of the frequencies used. Additionally, the system removes the need for any integrator or A/D convertor circuit, therefore, reducing not only cost and components, but also calibration requirements and system performance variations due to component tolerances. The improved measurement technique provides for improved reliability, scalability and tighter system tolerances for power control.

Figure 6:
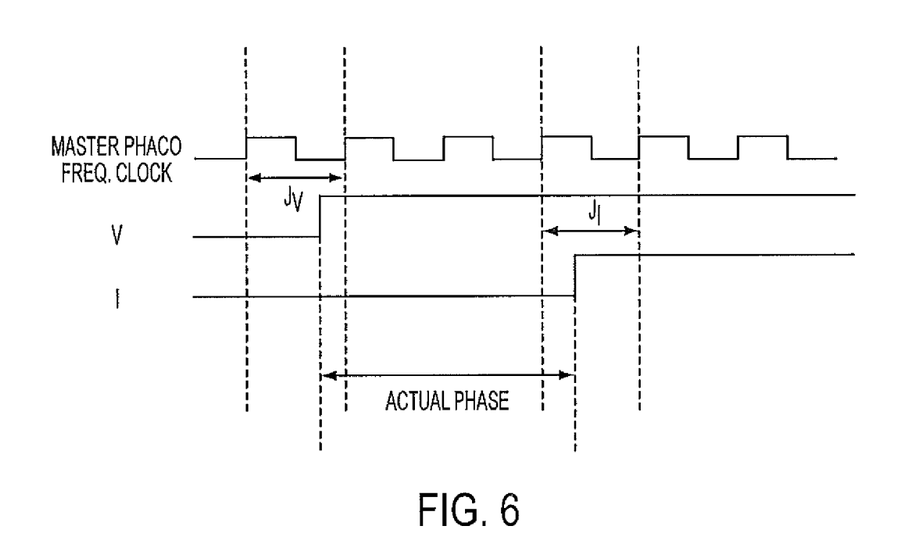
FIG. 6 is another timing diagram showing the relationship between the clock signal and the digital logic level signals to be measured.

In an alternative embodiment of the present invention, an improved phase detector additionally includes the steps of averaging multiple phase measurements. Averaging multiple phase measurements provides the benefit of filtering noise and jitter. Turning to FIG. 6, a sample diagram illustrating the timing of the digital logic level voltage waveform and current waveform are shown. The digital logic level voltage waveforms are obtained, as discussed above, using zero-cross detection circuits converting the sinusoidal AC signals into digital signals for processing. The period between the actual transitions of the logic level signals is presented as the actual phase to be measured between the signals.

Furthermore, a master phaco frequency clock, which is $2^N$ times faster, than the AC drive frequency where N represents between 2-16 bits used in system 100 as discussed above, is used to determine a time delta between the two signals. Despite the master phaco frequency clock running at an exponentially faster frequency than the AC drive signal, the transitions of the digital logic level signals may not occur on a transitioning edge of the master phaco frequency clock. This may occur, for example, where the digital logical level waveforms are asynchronous with the driving frequency. Accordingly, a single period of the master phaco frequency clock where the transition of the digital logic level signal occurs may define the jitter of the voltage and current transition measurement. With reference to FIG. 6, $J_V$ can be seen as the uncertainty of the AC voltage transition (i.e., the voltage jitter) and $J_1$ is shown to be the current jitter.

Therefore, in order to reduce jitter and other noise from the measurements, multiple phase measurements can be taken and averaged before any clock division. For example, using the higher speed master phaco frequency clock, the time delta between 8 voltage and current cycles can be added and divided by the 8 measurements to obtain a jitter-reduced time delta. This averaged time delta can then be used in division, as described above, to represent a 0 to 359 degree phase shift.

Figure 7:
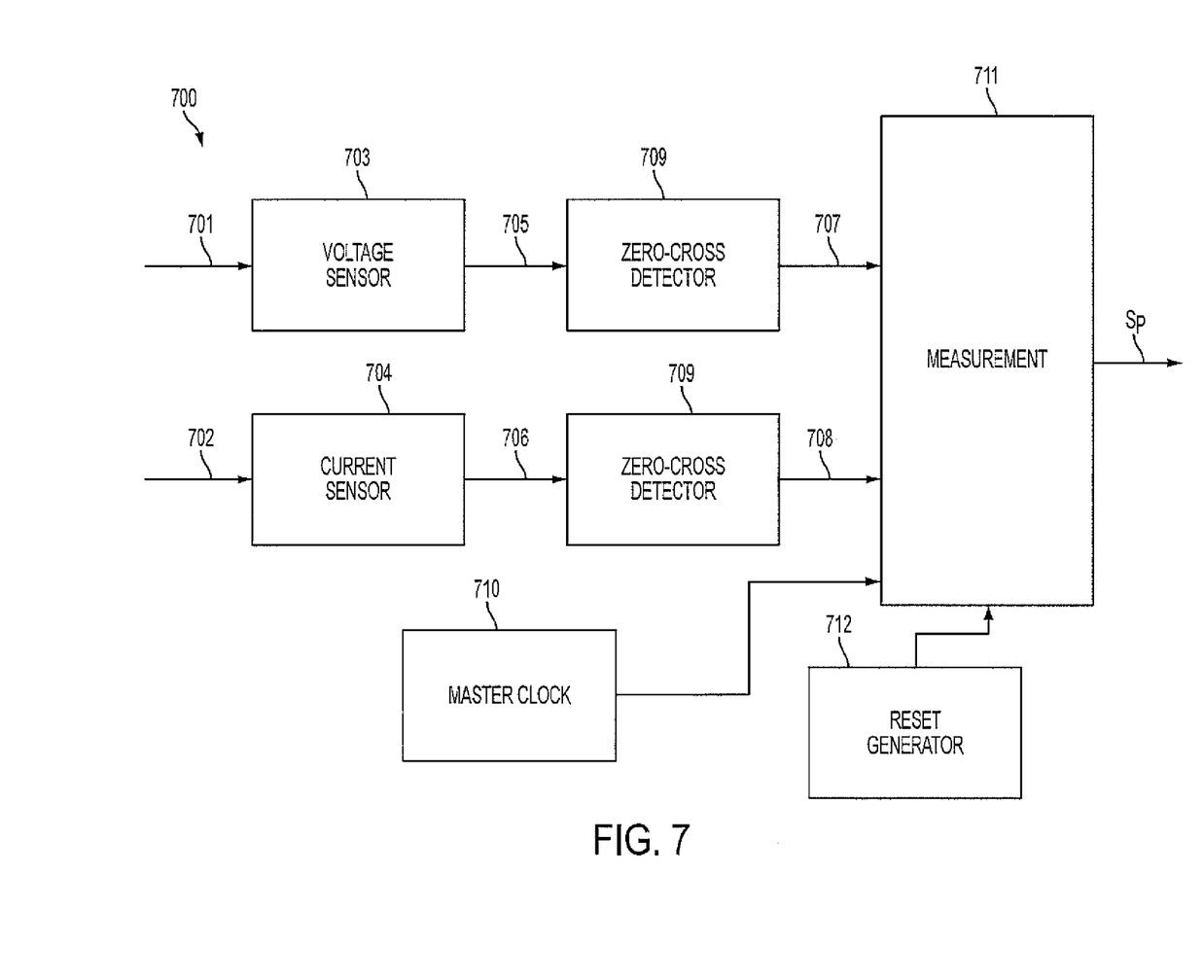
FIG. 7 is another functional block diagram of an improved phase measurement counter suitable for performing a method in accordance with the present invention.

Turning to FIG. 7, a preferred embodiment of a phase detection system 700 suitable for performing the method in accordance with the present invention is shown. Like with phase detector 400, the voltage input 701 and current input 702 from a phacoemulsification handpiece (not shown) are converted to appropriate signals using an attenuator 703 on the voltage signal to the phacoemulsification handpiece, and a current sense resistor 704 and fixed gain amplifier for the handpiece current. Thereafter, an AC voltage signal 705 and an AC current signal 706 are passed to zero-cross detectors 709 which convert the analog representations of the phacoemulsification voltage and current to digital signals 707, 708. Digital signals 707 and 708 represent a logical level square wave with transitioning edges at the AC zero value that can be measured within measurement circuit 711. A master clock 710 is fed into circuit 711 for timing of the phase measurement. The clock 710 uses a signal that is $2^N$ times faster than the frequency of the AC current signal where N represents between 2-16 bits used in system 100 as discussed above.

Upon a transition of a digital signal 707 representing an onset of a voltage cycle, measurement circuit 711 begins a counter to determine the time delta $S_P$ necessary for the digital signal 708 to transition representing the onset of a current cycle. The counter determines the number of higher speed clock 710 periods occurring between transitions of signals 707 and 708. This resulting time delta $S_P$ represents a phase measurement between the two AC waveforms.

The output $S_P$ is then fed to a system controller (not shown) that can divide the higher speed master clock to obtain the frequency of the operating phacoemulsification drive signals. Accordingly, dividing the higher speed clock to generate the ultrasonic clock ensures that the phase measurement is synchronous regardless of the driving frequency. This signal represents a measurement between 0 and 359 degrees of phase.

A reset generator 712 is also fed into circuit 711 to reset internal control signals within circuit 711 (not shown) and the master clock 710 upon completion of a phase measurement as discussed above.

Figure 8A:
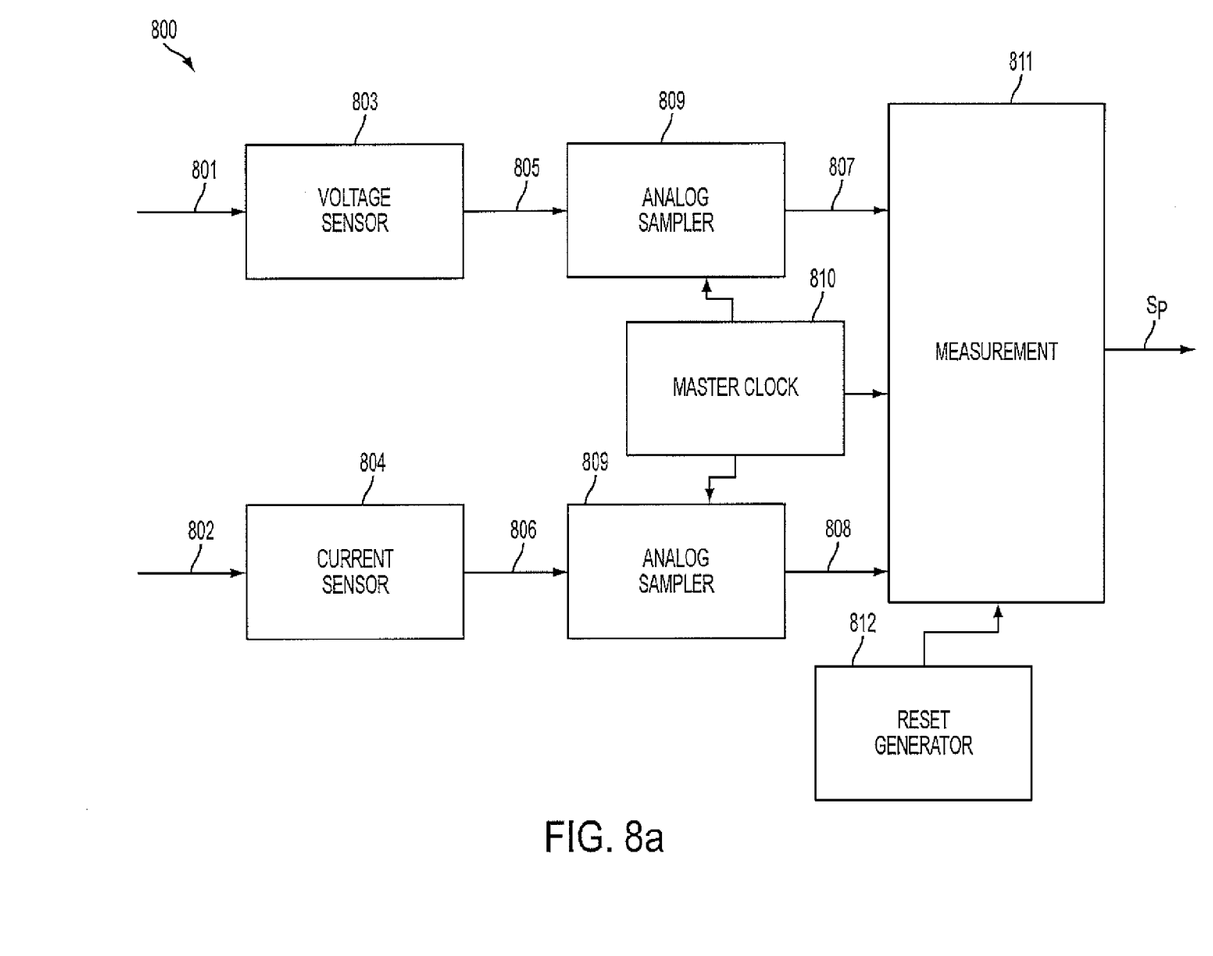
FIG. 8a is another functional block diagram of an improved phase measurement counter suitable for performing a method in accordance with the present invention.

Turning to FIG. 8a, yet another alternative embodiment suitable for performing the method in accordance with the present invention is shown. The previous embodiments are based on converting analog signals to digital signals using reference detection components as shown in FIGS. 4 and 7. However, other components may be utilized. For example, using a component with a sampling rate sufficient to digitally recreate an analog waveform may be used. Turning back to FIG. 8a, like with systems 400 and 700, system 800 begins with the voltage input 801 and current input 802 from a phacoemulsification handpiece (not shown). A voltage sensor 803 provides a voltage signal corresponding to the output voltage of the handpiece and a current sensor 804 provides a current signal corresponding to the output current. Thereafter, an AC voltage signal 805 and AC current signal 806 are passed to analog samplers 809 (e.g., analog converters), which convert the analog phacoemulsification voltage and current to discrete time digital representation signals 807, 808. For example, in one embodiment, an analog to digital converter ("ADC") with a sampling rate sufficient to recreate the analog signals may be used.

Figure 8B:
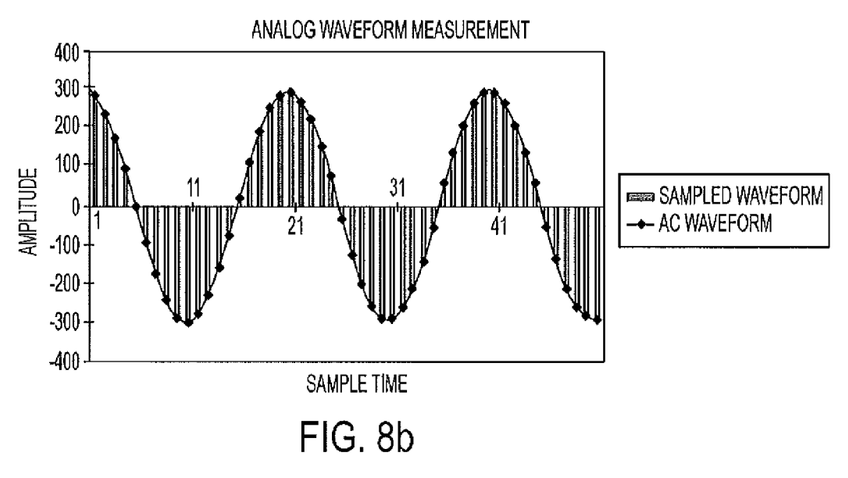
FIG. 8b is a diagram showing a representation of an analog signal as a digital signal.

With reference to FIG. 8b, an example of an analog waveform, for example, representing AC voltage or AC current, is shown sampled at a rate sufficient to construct a digital representation of the analog waveform based on amplitude measurements. Unlike systems 400 and 700, digitally reconstructing the analog waveforms introduces instantaneous analog information that can be used by measurement circuit 811 to improve resolution, reduce noise and avoid aliasing.

For example, the digital signals 807 and 808 can facilitate phase and amplitude measurements as discussed above. Similar to systems 400 and 700, signals 807 and 808 can be provided to measurement circuit 811. A master clock 810 is used for timing of the phase measurement. In one embodiment, the clock 810 uses a signal that is $2^N$ times faster than the frequency of the AC current signal where N represents between 2-16 bits used in system 100 as discussed above. This master clock 810 can be fed into either measurement circuit 811 or analog samplers 809 for timing of the phase measurement. In one embodiment, the master clock 810 drives the analog samplers 809 to determine the sampling rate of the analog signals. In an alternative embodiment, similar to FIGS. 4 and 7, using the digital signals 807 and 808, measurement circuit 811 begins a counter to determine the time delta $S_P$ between digital signals 807 and 808. The counter determines the number of higher speed clock 810 periods occurring between similar transitions of signals 807 and 808. With the analog information recreated in signals 807 and 808, the counter can provide a measurement that accounts for harmonic content, signal distortion information, and dynamic load characteristics that may affect phase measurements during operation.

The output $S_P$ is then fed to a system controller (not shown) that can divide the higher speed master clock to obtain the frequency of the operating phacoemulsification drive signals. Accordingly, dividing the higher speed clock to generate the ultrasonic clock ensures that the phase measurement is synchronous regardless of the driving frequency. Additionally, this division to obtain the desired sampling frequency using signals 807 and 808 aids in removing signal components with a higher frequency that may create undesirable noise, thereby alleviating aliasing concerns. This signal represents a measurement between 0 and 359 degrees of phase.

Furthermore, in another example, measurement circuit 811 can also measure energy and power during operation using the instantaneously sampled components of signals 807 and 808. As one of ordinary skill can appreciate, determining the product of the instantaneous current and voltage during operation can provide instantaneous power measurements, which can be fed to the measurement circuit 811 to calculate additional information such as true power and energy. Therefore, at any time during operation, recreating the analog signals in real-time offers the significant advantage of immediate and precise energy/power measurements.

A reset generator 812 is also fed into circuit 811 to reset internal control signals within circuit 811 (not shown) and the master clock 810 upon completion of a phase measurement, as discussed above, or completion of an energy and power measurement.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention may appropriately be performed using different or additional process actions, or a different combination or ordering of process actions. For example, this invention is particularly suited for measuring phase in phacoemulsification systems; however, the invention can be used for any system using phase angle as a tuning parameter. Additionally and obviously, features may be added or subtracted as desired. Accordingly, the invention is not to be restricted except in light of the attached claims and their equivalents.

What is claimed is:

1. A method for determining the voltage-current phase relationship of a piezoelectric phacoemulsification handpiece, said method comprising the steps of:
   obtaining an analog AC voltage signal corresponding to the operating AC voltage of a piezoelectric handpiece having a driving frequency;
   obtaining an analog AC current signal corresponding to the operating AC current of the piezoelectric handpiece;
   producing a digital representation of the AC current signal and the AC voltage signal using an analog detection circuit;
   correlating a reference amplitude component of the digital representation with a point in time using a master clock, wherein the master clock uses a signal that is faster than the driving frequency of the AC current signal;
   determining a phase count measurement, wherein the phase count is the number of master clock periods between the reference amplitude component of the AC current signal and the AC voltage signal; and
   resetting the master clock upon completion of the phase count measurement.

2. The method of claim 1, wherein the master clock has a frequency $2^N$ times faster than the driving frequency of the AC current signal, wherein N represents a number of digital bits.

3. The method of claim 2, further comprising dividing the phase count measurement by the $2^N$ factor to obtain a phase signal, wherein the division produces a measurement that is frequency independent and the phase signal corresponds to a 0 to 359 degree phase shift.

4. The method of claim 2, wherein the number of digital bits N represents 2-16 bits.

5. The method of claim 1, wherein the reference amplitude components are selected from the group consisting of a zero cross, a peak detection, and a trough detection.

6. The method of claim 1, further comprising the step of averaging a plurality of phase count measurements between said AC current signal and said AC voltage signal.

7. The method of claim 1, further comprising the step of measuring instantaneous power, the instantaneous power is based on one of the reference amplitude components.

8. A system for determining the voltage current phase relationship of a piezoelectric phacoemulsification handpiece comprising:
   a voltage sensor configured to obtain an analog AC voltage signal corresponding to the operating AC voltage of a piezoelectric handpiece having a driving frequency;
   a current sensor configured to obtain an analog AC current signal corresponding to the operating AC current of the piezoelectric handpiece;
   an analog detection circuit configured to produce a digital representation of the AC current signal and the AC voltage signal;
   a measurement circuit configured to correlate a reference amplitude component of the digital representation with a point in time using a master clock and to determine a phase count measurement, wherein the phase count is the number of master clock periods between the reference amplitude component of the AC current signal and the AC voltage signal, wherein the master clock uses a signal that is faster than the driving frequency of the AC current signal; and
   a reset generator configured to reset the master clock upon completion of the phase count measurement.

9. The system of claim 8, wherein the master clock has a frequency $2^N$ times faster than the driving frequency of the AC current signal, wherein N represents a number of digital bits.

10. The system of claim 9, further comprising circuitry configured to divide the phase count measurement by the $2^N$ factor to obtain a phase signal, wherein the division produces a measurement that is frequency independent and the phase signal corresponds to a 0 to 359 degree phase shift.

11. The system of claim 9, wherein the number of digital bits N represents is between 2 and 16 bits.

12. The system of claim 8, wherein the reference amplitude components are selected from the group consisting of a zero cross, a peak detection, and a trough detection.

13. The system of claim 8, further comprising circuitry configured to average a plurality of phase count measurements between said AC current signal and said AC voltage signal.

14. The system of claim 8, wherein the reference amplitude components comprise a plurality of sampled measurements sufficient to digitally recreate the analog waveform.

15. The system of claim 14, wherein said master clock determines the number of reference amplitude components.

16. The system of claim 14, further comprising circuitry configured to measure instantaneous power, the instantaneous power is based on one of the reference amplitude components.

17. A method for determining the voltage-current phase relationship of a piezoelectric phacoemulsification handpiece, said method comprising the steps of:

obtaining an analog AC voltage signal corresponding to the operating AC voltage of a piezoelectric handpiece having a driving frequency;

obtaining an analog AC current signal corresponding to the operating AC current of the piezoelectric handpiece;

producing a digital representation of the AC current signal and the AC voltage signal using an analog detection circuit;

correlating a reference amplitude component of the digital representation with a point in time using a master clock, the master clock having a frequency $2^N$ times faster than the driving frequency of the AC current signal, wherein N represents a number of digital bits;

determining a phase count measurement, wherein the phase count is the number of master clock periods between the transition of the digital representation of the AC current signal and the digital representation of the AC voltage signal;

dividing the phase count measurement by the $2^N$ factor to obtain a phase signal, wherein the division produces a measurement that is frequency independent and the phase signal corresponds to a 0 to 359 degree phase shift; and resetting the master clock upon completion of the phase count measurement.

18. The method of claim 17, further comprising the step of averaging a plurality of phase count measurements between said AC current signal and said AC voltage signal before the step of dividing the phase count.

19. The method of claim 17, wherein the reference amplitude components are selected from the group consisting of a zero cross, a peak detection, and a trough detection.

20. The method of claim 17, wherein the number of digital bits N represents is between 2 and 16 bits.

* * * * *